(12) United States Patent
Roitman et al.

(10) Patent No.: US 6,706,204 B2
(45) Date of Patent: Mar. 16, 2004

(54) METHOD OF FABRICATING AND A DEVICE THAT INCLUDES NANOSIZE PORES HAVING WELL CONTROLLED GEOMETRIES

(75) Inventors: Daniel B. Roitman, Menlo Park, CA (US); Dietrich W. Vook, Menlo Park, CA (US); Theodore I. Kamins, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 231 days.

(21) Appl. No.: 10/027,598

(22) Filed: Dec. 19, 2001

(65) Prior Publication Data

US 2003/0111440 A1 Jun. 19, 2003

(51) Int. Cl.[7] .............................. H01L 21/00; B44C 1/22
(52) U.S. Cl. .............................. 216/33; 216/56; 438/733
(58) Field of Search .................... 216/33, 56; 436/2, 436/151; 438/745, 752, 753, 733; 435/4

(56) References Cited

U.S. PATENT DOCUMENTS

| 5,013,337 A | 5/1991 | Bedard et al. |
| 5,795,782 A | 8/1998 | Church et al. |

Primary Examiner—William A. Powell (57) ABSTRACT

A method of fabricating nanosized holes with controlled geometries employs tools and methods developed in the microelectronics industry. The method exploits the fact that epitaxially grown film thicknesses can be controlled within a few atomic monolayers and that by using etching techniques, trenches and channels can be created that are only a few nanometers wide. The method involves bonding two shallow channels at an angle such that a nanopore is defined by the intersection. Thus, a nanopore-defining device includes a nanopore with dimensions that are determined by the dimensions and orientations of the intersecting channels, with the dimensions being accurately controlled within a few monolayers.

31 Claims, 9 Drawing Sheets

METHOD OF FABRICATING AND A DEVICE THAT INCLUDES NANOSIZE PORES HAVING WELL CONTROLLED GEOMETRIES

TECHNICAL FIELD

The invention relates generally to molecular detection and characterization and more particularly to fabricating reproducible, single-molecule nanopores having controlled geometric properties.

BACKGROUND ART

Devices and methods for detecting the passage of a single macromolecule through a nanopore are known. For example, U.S. Pat. No. 5,795,782 to Church et al. describes a nanopore that is created by the insertion of a bacterial pore-forming protein ($\alpha$-hemolysin) in a lipid membrane. Since protein geometry and physiochemical characteristics are genetically determined, the pore-forming protein is able to form nanopores having a predetermined geometry.

One concern with the prior art techniques is that the process of verifying the existence and proper formation of each nanopore fabricated by using bacterial pore-forming proteins is slow and potentially expensive. Another concern is that because the lipid membrane in which the nanopores are made degrades with time, the resulting nanopores cannot be mass produced for use over an extended period of time.

What is needed is a method for efficiently and consistently forming nanopores with controlled geometries such that the resulting nanopores can be formed in controlled arrays and are capable of being stored for extended periods of time without degrading. What is further needed is such a method that enables precise positioning of the nanopores.

SUMMARY OF THE INVENTION

Integrated circuit (IC) fabrication techniques are employed to form precisely dimensioned and positioned nanopores. Film-thickness control within a few atomic monolayers can be achieved by a variety of IC fabrication techniques, including photolithography, epitaxial growth and plasma enhanced chemical vapor deposition (PECVD).

A first embodiment of a method of forming nanopores uses a pair of three-layer segments. Each such multi-layer segment includes a substrate layer, such as a silicon substrate, and includes an intermediate layer and a top layer that are grown or deposited to predetermined and uniform thicknesses. The chemical compositions of the three layers are selected such that the substrate layer and top layer are selectively etchable with respect to the intermediate layer, while the intermediate layer is selectively etchable with respect to the substrate and top layers. In alternate embodiments, each layer is selectively etchable with respect to the other layers. Furthermore, it is contemplated that more than three layers are used to form the segments, with one or more of the layers being selectively etchable with respect the other layers.

The top layer of each three-layer segment is patterned so that at least one supply conduit extends through the top layer to the intermediate layer. Next, the intermediate layer of each segment is patterned using a wet etch process to remove a portion of the intermediate layer. This wet etchant is introduced through the supply conduit and the process is allowed to proceed sufficiently long to form an "undercut" in the intermediate layer, with the undercut extending beyond the boundaries of the supply conduit through the top layer.

Following the selective patterning of the top layer and the intermediate layer, excess matter is removed from the edges of each three-layer segment, so that at least one edge of the segment is smooth and is located at a controlled distance from the supply conduit. The smoothed edge is then masked with a photoresist, while leaving a controlled width of the intermediate layer exposed. A narrow slot in the intermediate layer along the smoothed edge of the segment is created using conventional photolithography and etching techniques. After etching, a second selective etch process is conducted to form a path in the intermediate layer from the undercut to the slot. Thus, the completed path within each segment extends from the supply conduit through the intermediate layer to the smooth edge of the segment.

To create a single nanopore, the slots of the pair of three-layer segments are abutted, with the axes through the slots being coaxial while the corresponding layers of the two segments are in non-parallel relationships. The segments are wafer bonded using known techniques. Finally, the exposed portions of the slots are filled. Thus, the resulting structure contains a single nanopore at the interface of the two segments. The geometry of the nanopore is controlled by the orientation of the two segments and the thicknesses of the intermediate layers.

Using modern microchip manufacturing techniques (e.g., epitaxial growth, PECVD, thermal growth, sputtering, evaporation or molecular beam epitaxy (MBE)), the thickness of the intermediate layer can be controlled to the nearest nanometer. Therefore, the dimensions of the resulting nanopore can also be controlled to the nearest nanometer. Furthermore, because the method of manufacture of the individual nanopores involves error-tolerant steps (i.e., process steps that achieve desired results despite process imperfections), both high batch yield and mass production are possible.

In the second embodiment, each of two multi-layer segments is etched to create a recess (or "tub") in its substrate layer. Preferably, the etching process is conducted such that the walls of the recesses intersect the front surface of the substrate layer at steep angles. The recesses are then etched so that the walls are smooth. A second selectively etchable material is blanket deposited or grown to a controlled thickness on each front surface and on the sides and bottom of each recess, thereby forming a coated tub. Each coated tub is then filled with a substance, such as the substrate layer material or a third etchable material. The upper surfaces of the segments are polished to a uniform level, typically past the original surface on which the second etchable material was blanket deposited or grown. As one example, the polishing of the segments may be performed using chemical mechanical polishing (CMP) to remove the materials (e.g., the second and third etchable materials) from the front surfaces of the segments. This step is error-tolerant, since polishing into the front surface of a segment does not adversely affect the process, providing the step leaves a "filled tub."

For each multi-layer segment, a portion of the second selectively etchable material on the upwardly extending side walls of the filled tub is masked and the exposed portion is at least partially etched. The surrounding substrate material may also be etched to facilitate etching of the second selectively etchable material. The resulting void is filled with a bonding material to bond the substrate to the "block" of material at the center of the recess. The mask is removed and the surface is again polished to a uniform level using polishing techniques known in the IC manufacturing art.

The two multi-layer segments having the same or different nanopore-defining patterns are then aligned such that the second selectively etchable layer of the first segment intersects the second selectively etchable layer of the second segment. The intersection satisfies predetermined geometric criteria. Specifically, the thicknesses of the walls of the tubs determine the area of the nanopore and the shape of the nanopore is determined by the wall thicknesses and by the orientations of the segments. Once aligned, the two segments are wafer bonded using techniques known in the IC manufacturing art.

The back of each multi-layer segment is etched to create a supply conduit. Each supply conduit is etched in a controlled manner from the back side of the segment in a position such that the supply conduit intersects the second selectively etchable layer of the segment. The second selectively etchable layer is then etched out of each segment, thereby creating a nanopore with predetermined dimensions and geometry. "Nanopore" is defined herein as including pores that have a cross sectional dimension as large as 0.1 millimeter.

An advantage of the invention is that nanopore capability is achieved using techniques that are conventionally considered to be inadequate for such purposes. Since film thicknesses are a key to setting the dimensions of the nanopores and since techniques for controlling film thicknesses to within a few atomic monolayers are known, "coarser" integrated circuit techniques (e.g., photolithography) may be employed for other steps without a sacrifice in end results. Another advantage is that the surfaces of the various channels can be easily modified to optimize their properties for the intended applications. For example, an oxide layer can be created in the channels by performing a baking step within an oxygen-rich environment or by performing anodic oxidation in order to adjust the surface charge for compatibility with DNA. The oxide layer can be further modified using well-known silalyation agents to add chemical functionality and to vary the degree of hydrophobicity. Moreover, the oxide layer can be modified to include affinity probes, such as Biotin and antibodies, enzymes, and/or surface-bound polymers. By tailoring the oxide layer to include agents and/or probes, the invention may be used in chemical analysis and characterization of macromolecules, synthetic and naturally occurring, colloidal micro and nanoparticles, based on interactions of such molecules and particles with the nanopore.

DETAILED DESCRIPTION

The following describes a method of fabricating one or more nanosize or microsize pores (i.e., "nanopores") with well controlled geometries and locations, as illustrated in FIGS. 1 through 14. The invention has two primary embodiments. Briefly, the first embodiment includes the steps of selectively etching portions of intermediate layers and top or bottom layers of a pair of three-layer segments. The edges of the two segments are then wafer bonded at a predetermined angle to each other, such that a single nanopore is formed at the segment-to-segment interface. The width of the nanopore is determined by the original thickness of the intermediate layer of the first segment. The height of the nanopore is determined by the original thickness of the intermediate layer of the second segment. The geometry of the nanopore is further controlled by the angle formed by the abutment of the two segments, which preferably is more orthogonal than parallel.

Figure 1:
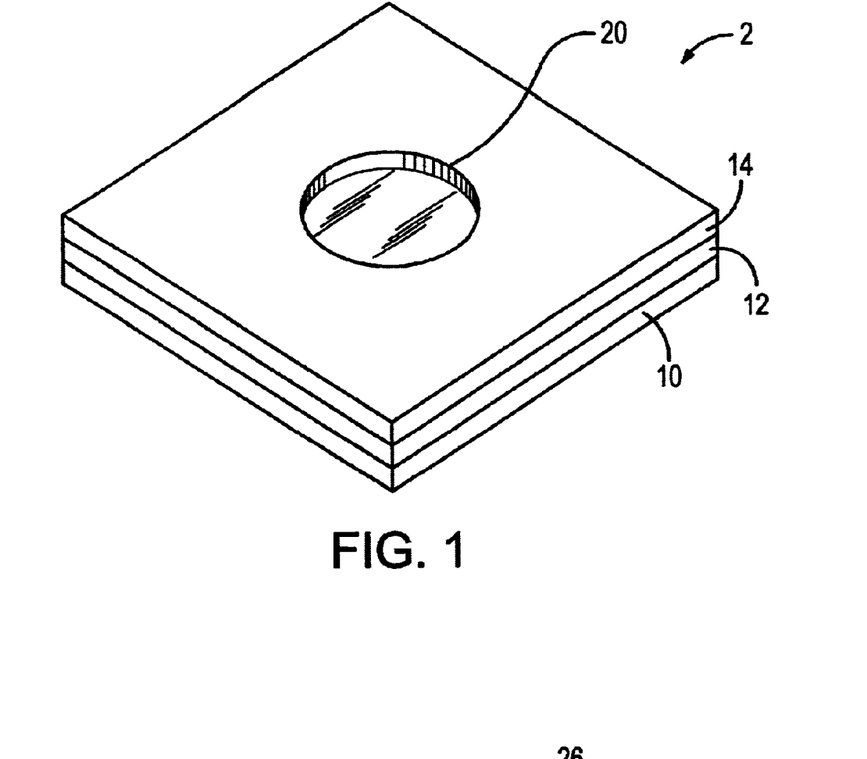
FIG. 1 is a perspective view of an exemplary three-layer segment having a supply conduit in accordance with a first embodiment of the invention.

FIG. 1 illustrates a single three-layer segment 2. The three-layer segment 2 is comprised of a substrate layer 10, an intermediate layer 12 and a top layer 14. While not critical, the substrate layer 10 may be a portion of a Silicon (Si) wafer that is standard to the integrated circuit (IC) manufacturing art. Providing the substrate is represented by step 30 in FIG. 3. The intermediate layer 12 is grown or deposited on the substrate layer 10 to a predetermined and uniform thickness, as shown in step 32. In the present embodiment, the intermediate layer 12 is composed of Silicon Germanium ($Si_xGe_{1-x}$, hereinafter SiGe) and is grown using techniques known in the IC manufacturing art. Thermal growth, epitaxial growth, sputtering, evaporation, PECVD, and MBE are all possibilities. Finally, the top layer 14 is deposited or grown on the intermediate layer 12 to a predetermined and uniform thickness using techniques known in the IC manufacturing art, as shown in step 34. In the present embodiment, the top layer 14 is composed of Si. Although the substrate layer 10 and the top layer 14 are stated as having known or predetermined and uniform thicknesses, this is not critical.

Additionally, although the substrate and top layers 10 and 14 are described as being Si and the intermediate layer 12 is described as being SiGe, this is not critical. The chemical compositions of the three layers 10, 12 and 14 should be selected such that the substrate layer 10 and top layer 14 may be selectively etched with respect to the intermediate layer 12, or the intermediate layer 12 may be selectively etched with respect to the substrate and top layers 10 and 14. Thus, materials in the III-V system, as known in the IC manufacturing art, or other materials such as polymers, glasses and insulators, could be used to form the three-layer segment 2. In alternate embodiments, the materials for the three layers may be selected such that each layer is selectively etchable with respect to the other two layers. It is also contemplated that more than three layers may be used to form the segment of FIG. 1, with each layer being selectively etchable with respect to the other layers.

Once the three-layer segments are formed, the top layer 14 of each three-layer segment 2 is patterned at step 36 by etching at least one supply conduit 20 to extend through the top layer 14 or the substrate layer 10 to the intermediate layer 12. In the present embodiment, the etched supply conduit 20 is approximately 50 μm in diameter, but this is not critical. Moreover, this step is error-tolerant, since neither the exact position nor the exact dimensions of the supply conduit are critical to the performance of the final product. A selective etch of the top layer 14 may be performed using a mixture of $HNO_3$, HF and acetic acid. Nevertheless, selective etching of the top layer 14 may be performed using any etching process known in the IC manufacturing art which allows selective etching of the top layer 14 with respect to the intermediate layer 12. Furthermore, although in this embodiment the supply conduit 20 is etched through the top layer 14, in alternative embodiments, the supply conduit 20 may be formed by etching the substrate layer 10.

Figure 2:
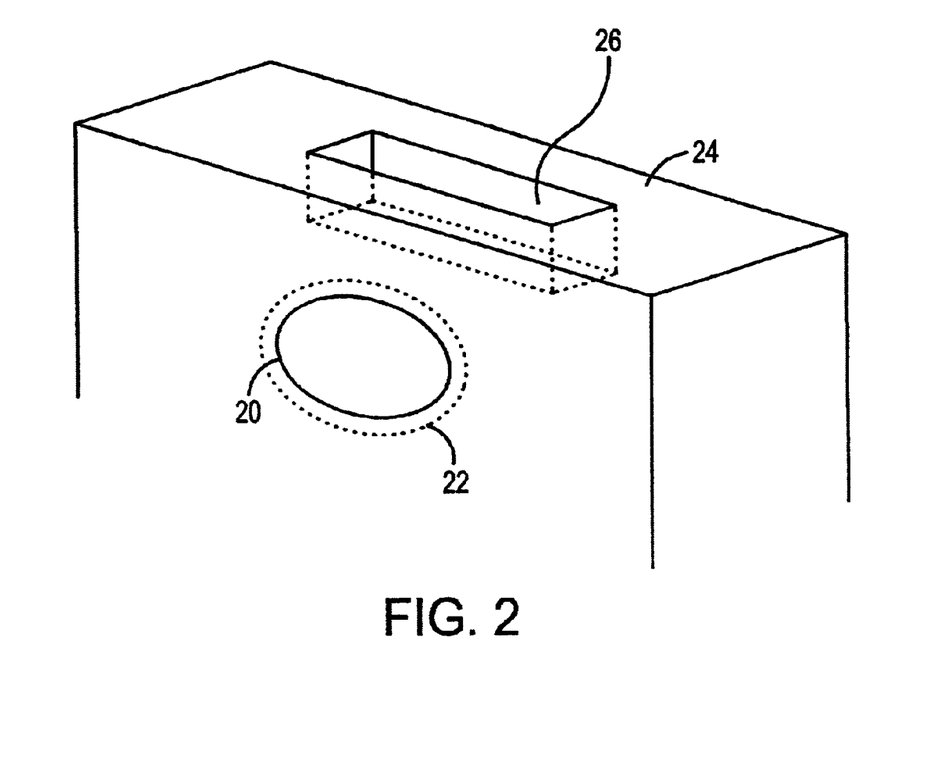
FIG. 2 is a perspective view of the three-layer segment of FIG. 1 having the supply conduit, an undercut and a slot in a smoothed edge.
Figure 3:
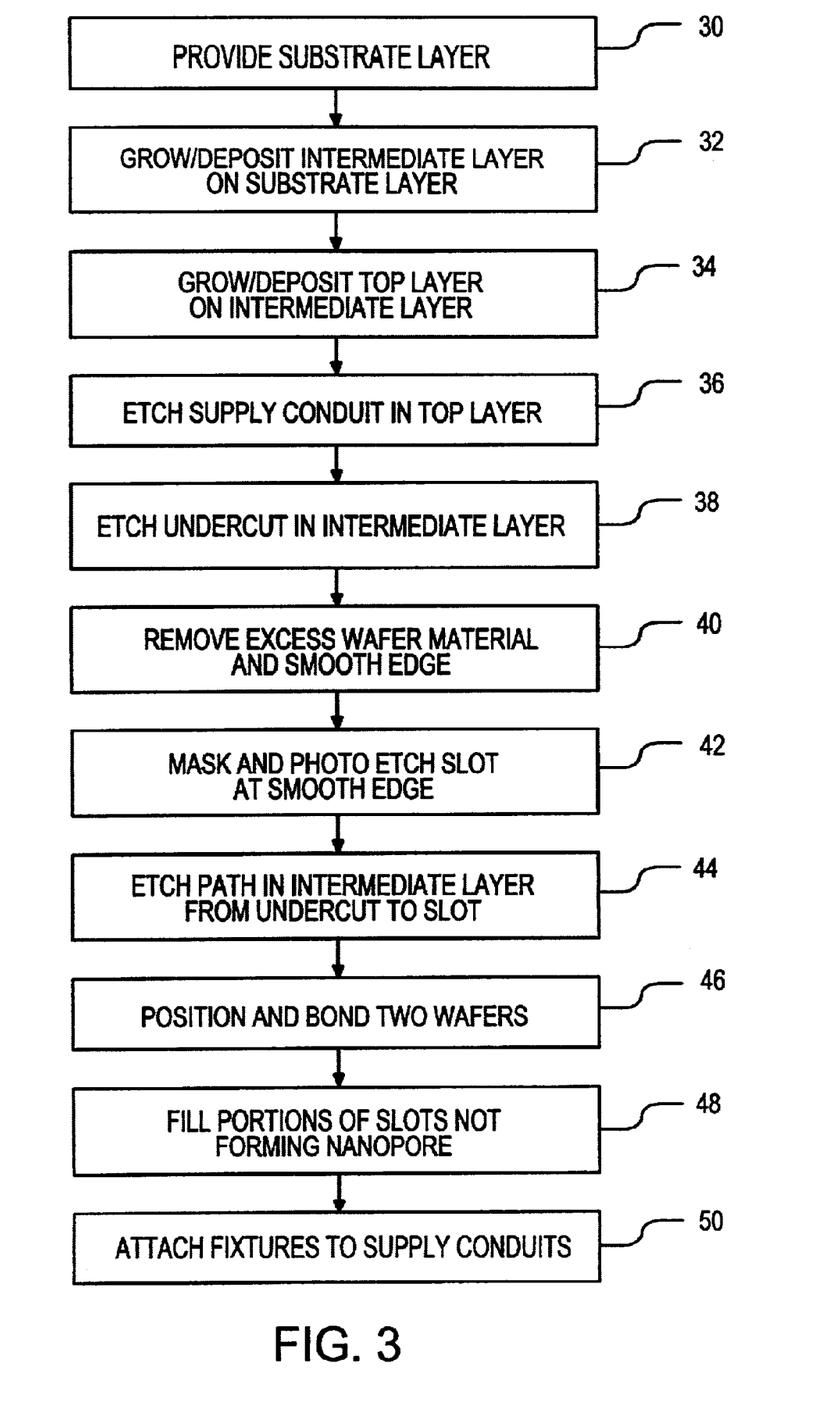
FIG. 3 is a process flow for manufacturing a single nanopore having a well controlled geometry in accordance with the first embodiment.

With reference to FIG. 2 and FIG. 3, after etching the supply conduit 20, the intermediate layer 12 of each three-layer segment 2 is selectively time etched using a wet etch process at step 38, as known in the IC manufacturing industry. The wet etch process is performed such that a portion of the intermediate layer 12 is removed in a pattern that is defined by the shape of the supply conduit 20. The process continues sufficiently long to allow an undercut 22 to form in the intermediate layer 12. The "undercut" is that portion of the etched region which extends beyond the boundaries of the supply conduit 20 in the top layer 14. While etching of the undercut 22 is described as being performed using a wet etch process, this is not critical. Any etch process that selectively etches the intermediate layer 12 with respect to the top layer 14 and the substrate layer 10 may be employed. Because the exact dimensions of the undercut are not critical, performance of step 38 is error-tolerant.

At step 40, excess matter of the three-layer segment 2 is removed from the perimeter of the segment such that at least one edge of the segment 2 is smooth and is at a controlled distance from the supply conduit 20. In the present embodiment, the distance from a smooth edge 24 to the boundary of the supply conduit 20 is 100 μm, however this distance is not critical. The removal of matter and smoothing of the edge of the segment may be accomplished by sawing the segment and using Chemical Mechanical Polishing (CMP), as known in the IC manufacturing art. However, any method known in the IC manufacturing art that will produce a smooth edge 24 at a controlled distance from the undercut 22 may be employed.

Figure 4:
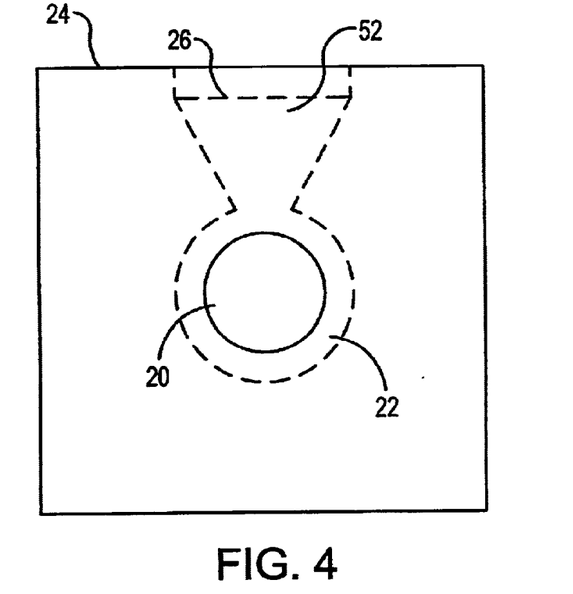
FIG. 4 is a front view of the three-layer segment of FIG. 2 having a path from the undercut to the smoothed edge.

The smooth edge 24 is masked at step 42 with a patterned photoresist to expose at least a portion of the length of the intermediate layer 12. In the present embodiment, the length of the exposed intermediate layer 12 is on the order of 100 μm, however this dimension is not critical. A slot 26 in the intermediate layer 12 at the smooth edge 24 is created using conventional photolithography combined with selective etching techniques. The slot has a width dimension (e.g., w=100 μm) perpendicular to the thicknesses of the three layers 10, 12 and 14, where w is precisely controlled to the resolution of the selected photolithography techniques (100 nm to 1 μm). The slot has a depth, or thickness, dimension (d) measured in the direction parallel to the thicknesses of the three layers, where d is precisely controlled by the selected techniques for forming the intermediate layer (1 nm to 10 nm). With reference to FIGS. 3 and 4, after the slot is completed, a second selective etch process is performed at step 44 to form a path 52 in the intermediate layer 12 from the slot 26 in the smooth edge 24 to the undercut 22.

Figure 5:
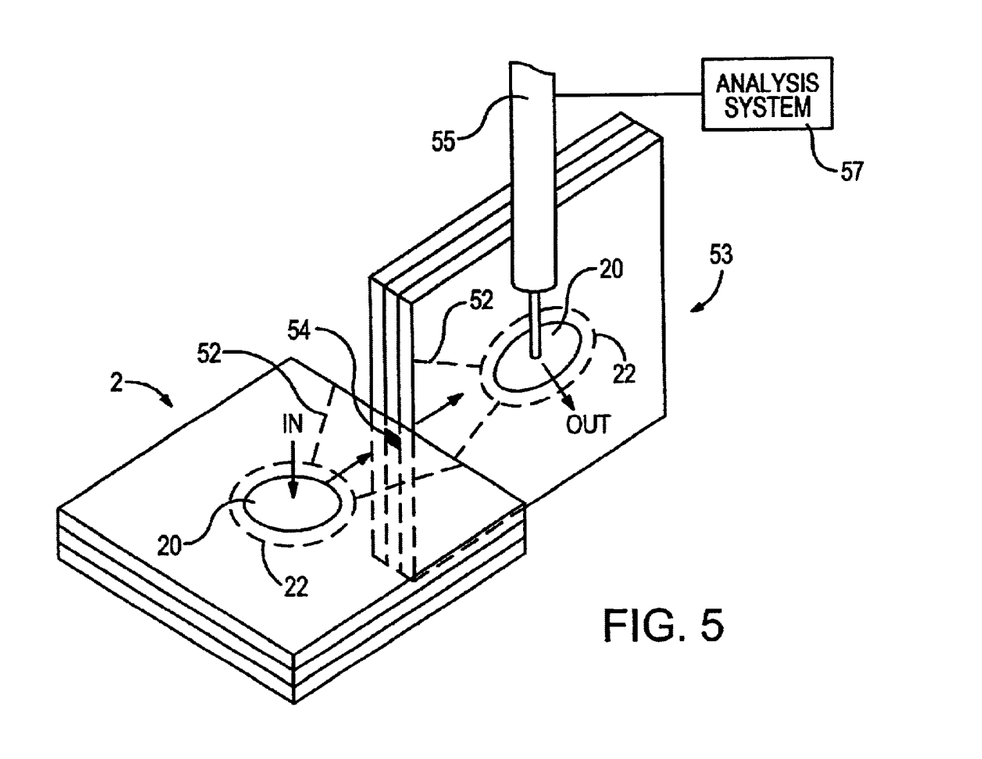
FIG. 5 is a perspective view of a pair of three-layer segments of FIG. 3 abutted in a non-parallel manner, thus creating a single nanopore.

In reference to FIGS. 3–5, a pair of three-layer segments 2 and 53 are oriented in a non-parallel manner, such that the interface of the slots 26 in the pair of three-layer segments forms a single nanopore 54 (which is represented by a black region). In step 46, the segments are abutted and wafer bonded using aligning and wafer bonding techniques known in the IC manufacturing art. If the widths (w) of the slots 26 exceed the thickness of the three layers 10, 12 and 14 that form each segment 2 and 53, it may be necessary to fill the portions of the slots that are not part of the nanopore 54 with a bonding material, as shown in step 48. Thus, when in use, matter will only proceed from the etched path 52 of the first segment 2 to the etched path of second segment 53 via the resulting nanopore 54. Filling the portions of the slots 26 that are not part of the nanopore 54 may be performed using a thermoset or photocurable polymer or using other techniques known in the IC manufacturing art, such as PECVD or sputtering. The geometry of the nanopore 54 is controlled by the orientation of the three-layer segments relative to each other and the thicknesses of the intermediate layers of the two segments. In a preferred application, the segments 2 and 53 are at right angles to each other and the slots are 20 μm features, but some applications may benefit from segment alignments between zero and ninety degrees.

At step 50, fixtures (i.e., plumbing) may be attached to the supply conduits 20 of the three-layer segments 2 and 53 to enable the introduction and exit of matter passed through the nanopore 54, as indicated by the flow arrows in FIG. 5. A probe 55 and an analysis system 57 are schematically shown to represent the use of the device. The device may be used for DNA sequencing, for example, by performing DNA injection at the IN supply conduit and monitoring properties within the OUT supply conduit. Ideally, properties (e.g., conductivity) are monitored within the nanopore 54 itself, but this is not an issue in all applications.

FIGS. 6 through 14 illustrate the second embodiment of the invention. In reference to FIG. 6 and FIG. 7, a substrate layer 90, such as a Si substrate, is provided (step 60) and patterned (step 62). The pattern into the substrate layer should have the appropriate angles and orientation to follow the crystal planes of the substrate material. As an example, for a Si substrate layer with a (110) orientation, the angle should be approximately 109 degrees.

Figure 7:
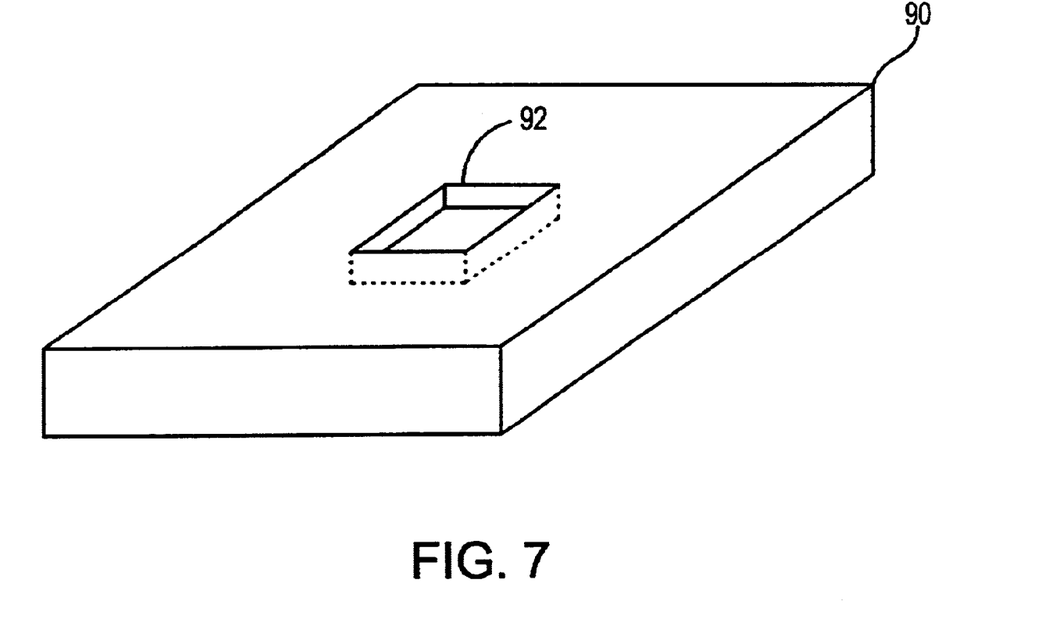
FIG. 7 is a perspective view of a substrate layer having an etched recess in accordance with the method of FIG. 6.

In step 62, a recess 92 is etched in the substrate layer 90 to a predetermined depth using etching techniques known in the IC manufacturing art. In the preferred embodiment, each recess in an array of recesses is etched to a depth of approximately 100 μm using a KOH etch process. Also in the preferred embodiment, the recesses have sides of approximately 100 μm. However, the depth of the etch, the dimensions of the pattern, and the etch process are not critical. Etching is conducted such that the walls of the recesses intersect the plane of the front surface 98 at steep angles. It should be noted that while only one substrate layer 90 is shown in FIG. 7, a second substrate layer (e.g., a second Si substrate) is similarly processed.

The recesses 92 in both substrate layers 90 are then cleaned at step 64, so that the walls of the recesses are smooth. Cleaning of the recesses can be accomplished by any means known in the IC manufacturing art.

Figure 6:
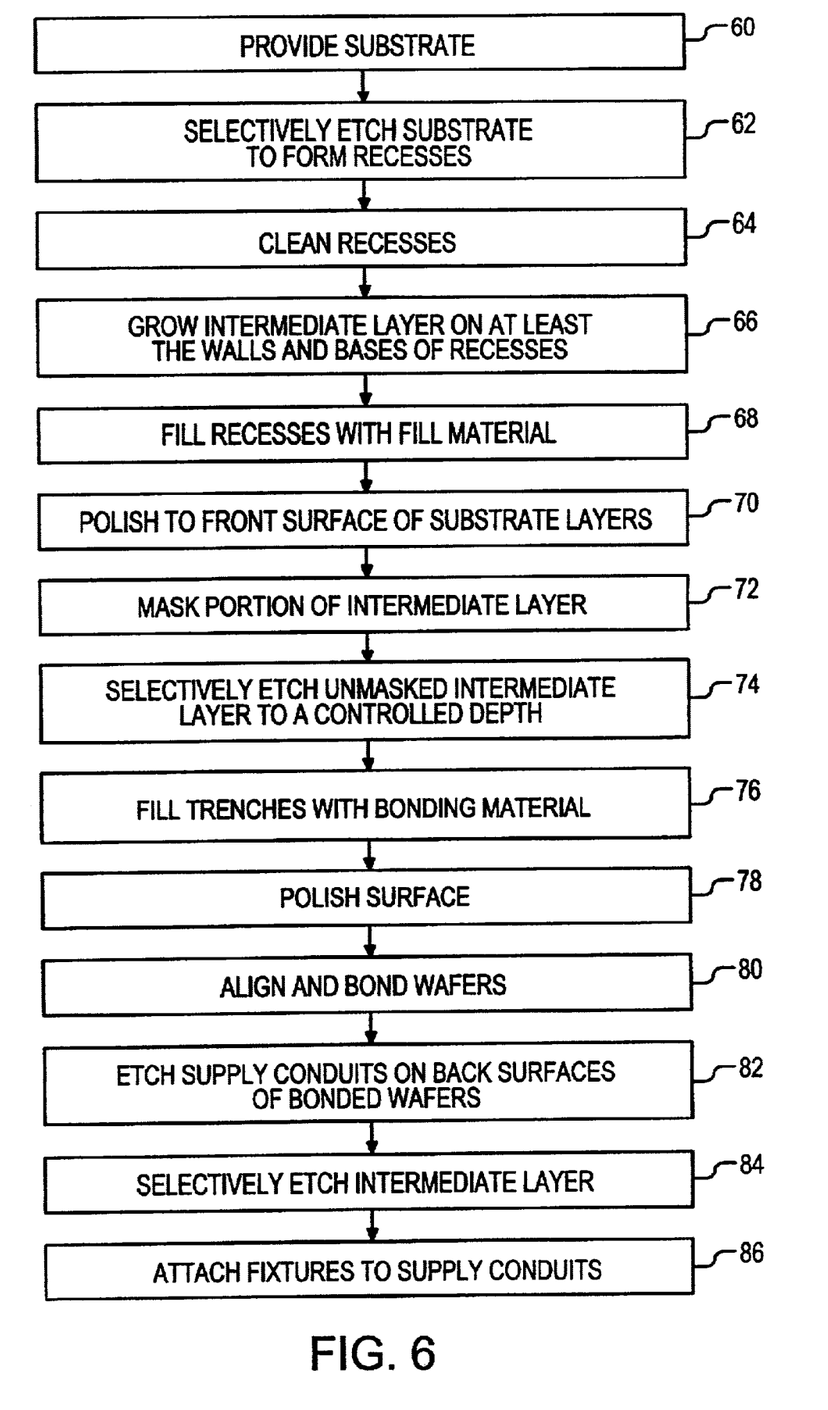
FIG. 6 is a process flow for manufacturing a nanopore having a well controlled geometry in accordance with a second embodiment of the invention.
Figure 8:
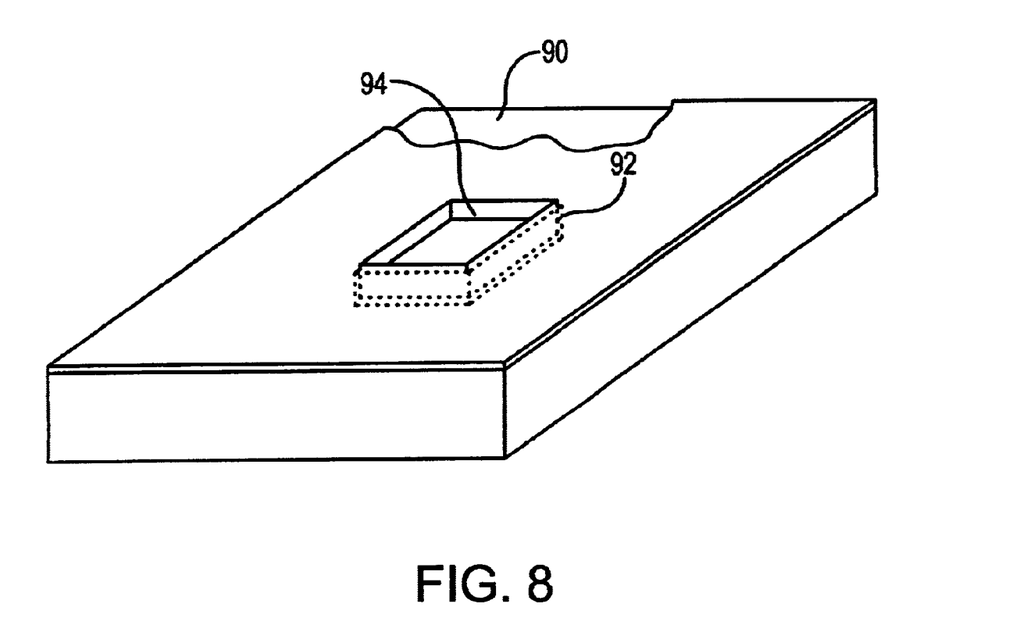
FIG. 8 is a perspective view of the substrate layer of FIG. 7 having an intermediate layer.

In reference to FIG. 6 and FIG. 8, a thin intermediate layer 94 of SiGe is then grown at step 66 on at least the walls and base of the recess 92 of both substrate layers. In the preferred embodiment, the SiGe layer is grown to a controlled thickness of 2 nm within each recess and on the front surface of each substrate layer (i.e., a blanket deposition). However, selective deposition to merely coat the recesses may be achieved by covering the front surfaces with a sacrificial oxide during the SiGe growth, with the sacrificial oxide being removed at a later time (step 70). As will be explained below, the thickness of the intermediate layer 94 plays an important role in determining the dimensions of the nanopore to be formed. However, it is not critical that the intermediate layer 94 be 2 nm thick, nor is it critical that intermediate layer 94 be composed of SiGe. The thickness of the intermediate layer 94 should be determined by the size of the desired nanopore, and any material that is selectively etchable with respect to the substrate layer 90 may be used.

In reference to FIG. 6, each recess 92 is then filled in step 68 with Si, Poly-silicon or any other material selectively etchable with respect to the intermediate layer 94. Similar to forming the intermediate layer in step 66, the material is preferably blanket deposited or grown at step 68. However, if the sacrificial oxide was used to limit the growth of the intermediate layer to a coating of the recess, the same sacrificial oxide will limit the growth at step 68 to growth within the recess.

Figure 9:
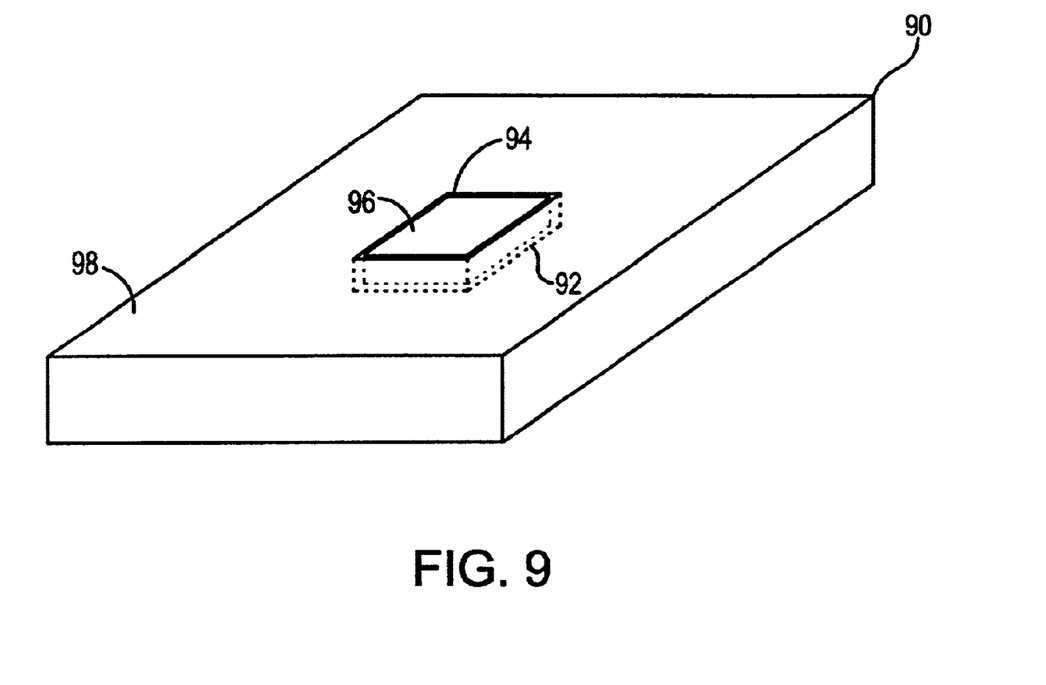
FIG. 9 is a perspective view of the substrate layer of FIG. 8 having material formed within the recess.

Referring now to FIGS. 6 and 9, the top of each multi-layer segment is polished in step 70, such that the substrate layer is coplanar with the intermediate layer 94 and a "block" 96 within the recess 92, where the "block material" is the material that was grown or deposited in step 68. In the preferred embodiment, CMP is used to polish the segments, but this is not critical. This step is error-tolerant, since over-polishing into the substrate layer will not affect performance of the end product.

Figure 10:
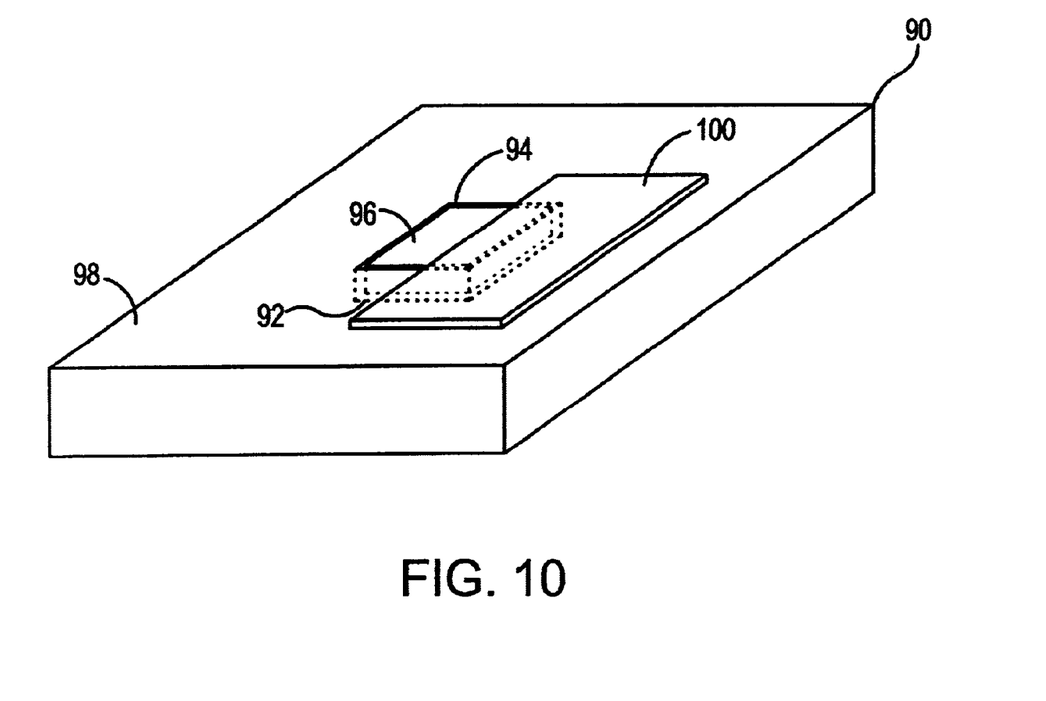
FIG. 10 is a perspective view of the substrate layer of FIG. 9 wherein a portion of the intermediate layer is masked.

In reference to FIG. 6 and FIG. 10, a portion of the intermediate layer 94 that is exposed at the front surface 98 of the substrate layer 90 is masked at step 72 with an etch resistant mask 100. In the preferred embodiment, the intermediate layer 94 is masked to expose all but a "C" shape of the SiGe intermediate layer. As will be explained below, it is the protected portion that is used to form the nanopore. The unmasked portion of the intermediate layer 94 is etched at step 74 to a depth of approximately 10 μm. Additionally, a portion of the surrounding substrate layer 90 may be etched during the etching of the intermediate layer material. Again, the process is error-tolerant. The mask 100 may then be removed.

At step 76, the resulting trench in the SiGe material is filled with "bonding material" 102 (FIG. 11) to attach the block 96 to the substrate layer 90. This prevents the block from "floating" after the nanopore-fabrication process is complete. In one embodiment, the bonding material 102 is silicon or Poly-silicon. However, any material that is capable of bonding the substrate layer 90 to the block 96 may be used. It should be noted that although the etch is described as being performed to a depth of 10 μm, this is not critical. The selective etch need only be sufficiently deep such that when the void is filled, the resulting bond has sufficient strength to secure the block in place relative to the substrate layer after the front surface 98 is again polished to a uniform level using CMP. In reference to FIG. 6 and FIG. 11, upon completion of this second polishing step 78, the front surface 98 is smooth, but has an exposed channel 104 of SiGe in a "C" shape. For clarification, the SiGe intermediate layer is shown by hatching.

Figure 11:
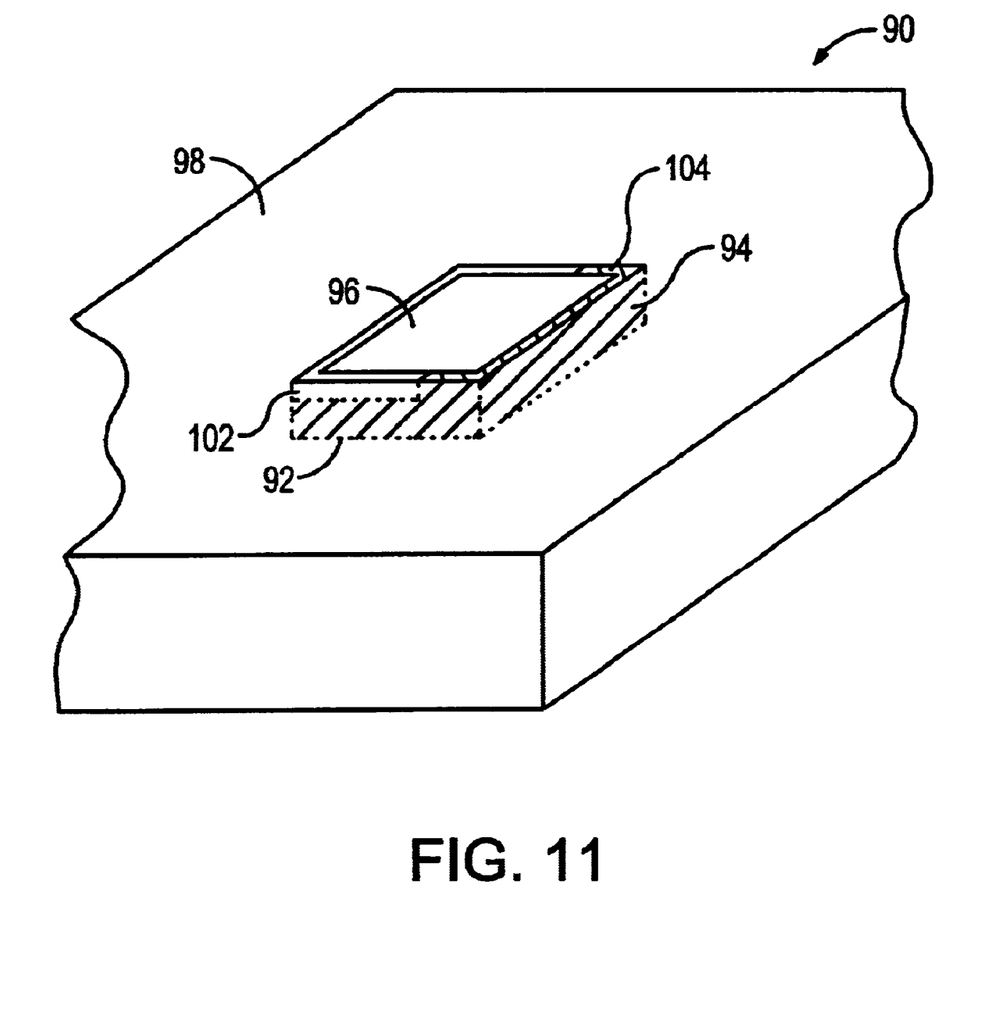
FIG. 11 is a perspective view of the substrate layer of FIG. 10 wherein a portion of the intermediate layer has been etched out and filled.

At step 80, first and second multi-layer segments are aligned and wafer bonded. The alignment of the blocks 96 and 106 of the two segments is isolated in FIG. 12, while the alignment of the exposed SiGe channels 104 and 108 is isolated in FIG. 13. The alignment of the blocks 96 and 106 provides one location 110 at which the SiGe channel 104 of the lower block 96 contacts the SiGe channel 108 of the upper block 106. It is at this location 110 that the nanopore will subsequently be formed. The portion of the SiGe that is covered by the bonding material following the etch-and-fill process described with reference to FIGS. 10 and 11 is not shown in FIG. 13, since it is not exposed. Thus, only one nanopore will be formed. As can be seen from FIG. 13, the alignment does not need to be precise, since the channels 104 and 108 will overlap even if they are not centered relative to each other.

Figure 14:
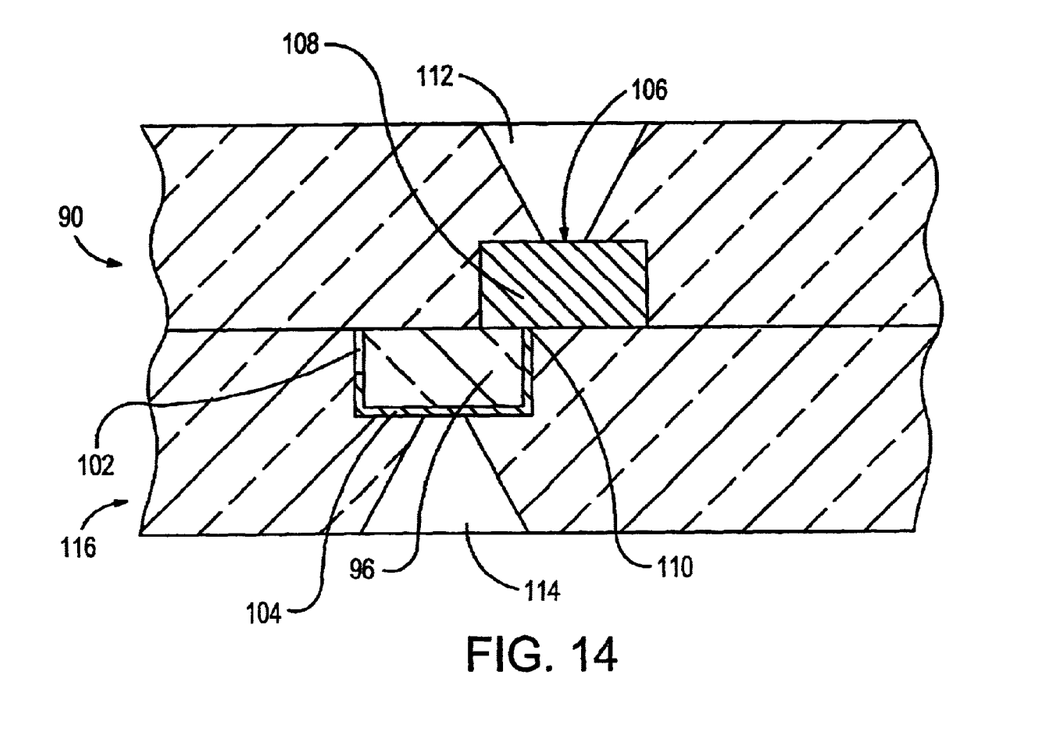
FIG. 14 is a side sectional view of supply conduits and intermediate layers of multi-layer segments formed in accordance with the method of FIG. 6.

In step 82, supply conduits are etched from the back sides of the two bonded segments. This is represented in FIG. 14. In this figure, the supply conduits 112 and 114 have been completed, but the SiGe material of the exposed channels 104 and 108 remains. The etching of the supply conduit 112 through the upper segment 90 will be described, but the same process is followed in forming the supply conduit 114 through the lower segment 116. As one possible approach, a selective KOH etch step is allowed to anisotropically etch the silicon of the substrate layer 90. The etch progresses at least until the block 106 is reached. Because of the configuration of the SiGe material, the etching will intersect the SiGe without requiring exacting tolerances in the location of the etching.

In another approach to the etching process, the size of the hole at the back side of the substrate layer is set to create an etch pit that will stop within 100 μm of the front surface of the substrate layer. As a consequence, the etch will stop within 20 μm to 50 μm of the portion of the SiGe that is parallel with the front surface of the substrate layer. This only partially completes the formation of the supply conduits. Next, the hole is etched with a non-selective etchant, until the supply conduit reaches the SiGe sidewall as shown in FIG. 14. Again, the tolerances are relaxed, since significant over etching can occur without adversely affecting the process.

Figure 13:
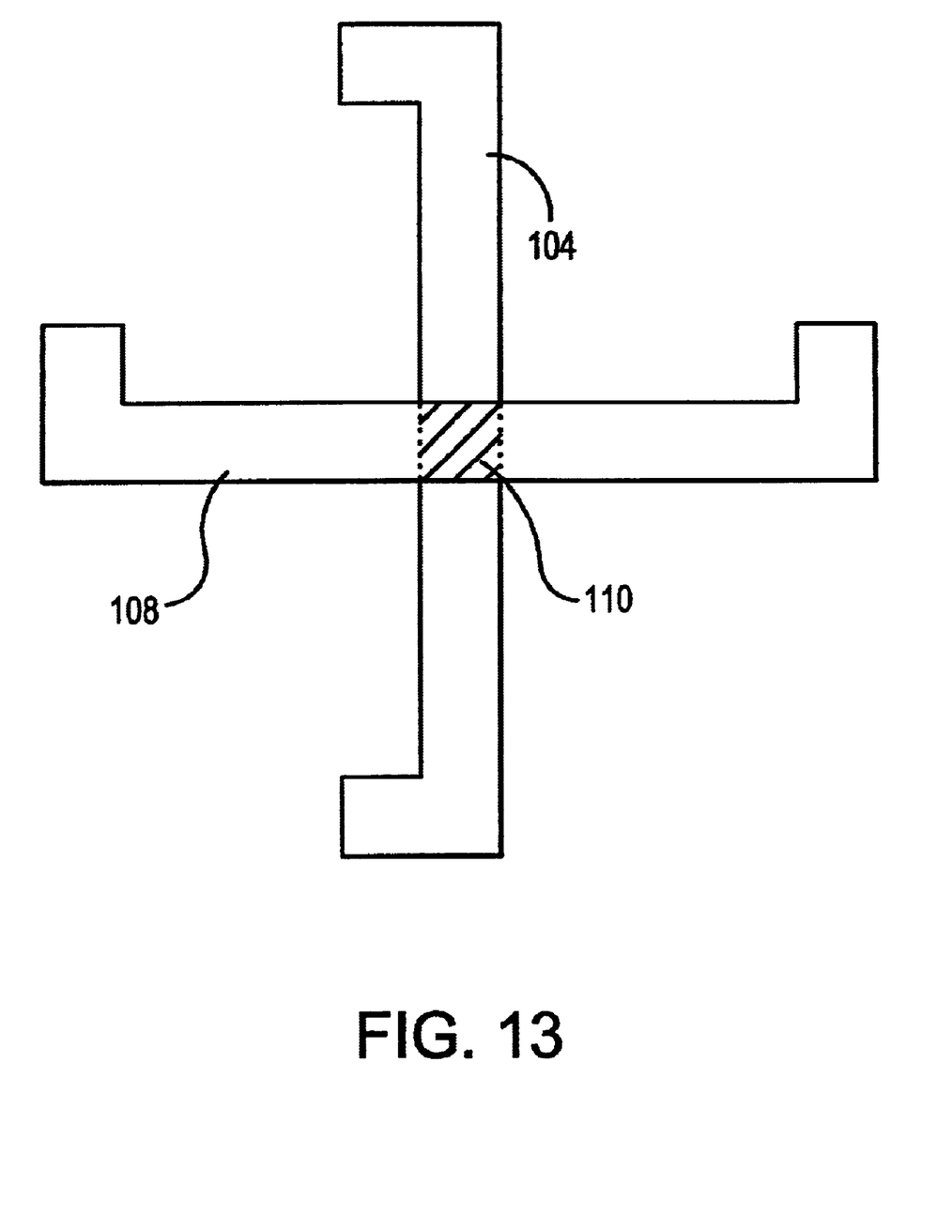
FIG. 13 is a top view illustrating the overlap of two channels of FIG. 12, thereby defining the position of a single nanopore.

The SiGe material is then etched at step 84. As a result, the supply conduit 112 is connected to the supply conduit 114 via the channels 104 and 108 that previously contained the SiGe material. Referring to FIGS. 13 and 14, the connection between the two supply conduits will have dimensions that are dictated by the dimensions and the alignment of the exposed channels 104 and 108. For the nanopore location 110 in which the exposed channels intersect at right angles and have a thickness of 2 nm, the nanopore will have a square cross section of 2 nm×2 nm. However, other dimensions may be more desirable in specific applications.

In step 86 of FIG. 8, plastic moldings or plumbing fittings are glued or otherwise attached to the two segments of FIG. 14. The moldings or plumbing fittings provide fluidic connections to the supply conduits 112 and 114. The device may then be used in a manner that was described with reference to FIG. 5. As an alternative to the fabrication sequence in which the supply conduits are first etched and then attached to moldings or plumbing fittings, the steps can be reversed. Within this alternative approach of attaching the moldings or plumbing fittings and then etching the supply conduits, the attached moldings/fittings are effectively defining the etching regions.

Figure 12:
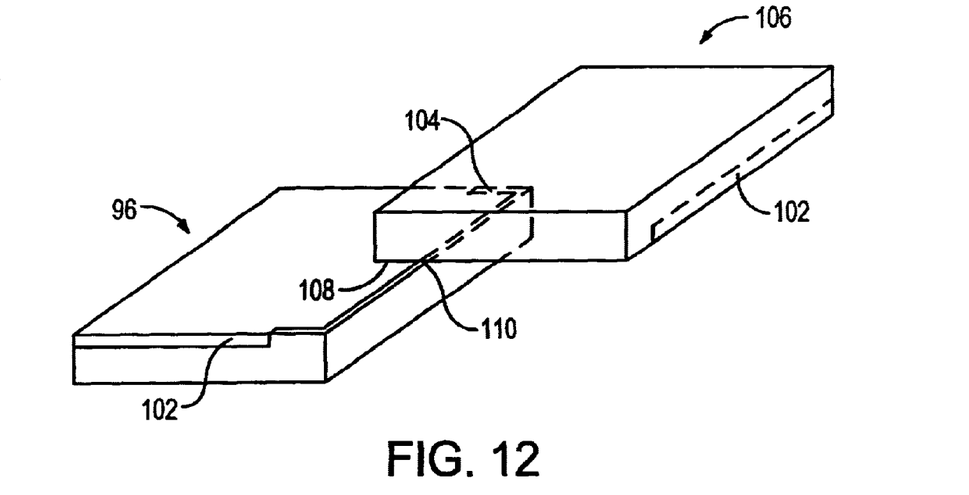
FIG. 12 is a perspective view of the alignment of the intermediate layers of two multi-layer segments in accordance with the method of FIG. 6.

While the second embodiment of FIGS. 6–14 has been described as being one in which a single "block" is formed in each multi-layer segment, the process is easily adapted to forming an array of nanopores. That is, a number of blocks can be formed in a first segment and a corresponding number of slightly offset blocks can be formed in a second segment, so that the arrangement of FIGS. 12, 13 and 14 is repeated across the surfaces of the segments when the two segments are aligned and bonded. The pattern of nanopores may be selected for use in array-based nanopore DNA sequencing or similar processing.

As an optimal feature for either or both of the embodiments described above, the surfaces of the channels can be modified to tailor their properties for the intended applications. For instance, an oxide layer can be formed in the channels by performing a bake in an oxygen-rich environment or by performing anodic oxidation. The oxide layer will vary the surface charge for compatibility with DNA. The oxide layer can be further modified using well-known silayation agents to add chemical functionality and to vary the degree of hydrophobicity. As another possibility, the oxide layer may be modified with affinity probes, such as Biotin and antibodies, enzymes, and surface-bound polymers.

The devices that are formed using the process steps that have been described will have well-defined arrays of holes in the nanometer to micron range. While the method has been described as used to provide holes that are in the nanometer range, "nanopore" is defined herein as including holes which have dimensions as great as 0.1 millimeter.

What is claimed is:

1. A method of manufacturing pores having controlled geometries and locations comprising the steps of:
    forming a first channel in a first member, including using fabrication techniques that enable formation of a first channel-defining layer having a well controlled thickness and including removing at least a region of said first channel-defining layer to form said first channel so as to have a controlled geometry in a thickness direction of said first channel-defining layer;
    forming a second channel in a second member, including using said fabrication techniques to form a second channel-defining layer having a well controlled thickness and including removing at least a region of said second channel-defining layer to form said second channel so as to have a controlled geometry in a thickness direction of said second channel-defining layer;
    positioning said first member relative to said second member such that said first channel is in alignment with said second channel in at least one location, thereby defining a location of said pore; and
    enabling fluid communication between said first and second channels via said pore.

2. The method of claim 1 wherein each said step of forming said first and second channels includes forming an exterior region having a sequence of layers and includes removing at least a portion of an interior layer of each said sequence to define said first and second channels, each said first and second channel having a longitudinal dimension that is perpendicular to a thickness of said interior layer that was removed, said step of positioning said first member including aligning said first and second channels such that said longitudinal dimensions are non-parallel, said pore having dimensions determined by said thicknesses of said interior layers and by a non-parallel relationship of said first channel relative to said second channel, said interior layers of sequences being said first and second channel-defining layers.

3. The method of claim 1 wherein said step of forming said first channel comprises the steps of:
    providing said first member as a first multi-layer segment having a first substrate layer;
    forming said first channel-defining layer having said well controlled thickness on a top surface of said first substrate layer;
    forming a first top layer having a controlled thickness on a side of said first channel-defining layer opposite said first substrate layer;
    selectively removing a portion of at least one of said first substrate layer and said first top layer, thereby creating a first supply conduit; and
    forming a first path through said first channel-defining layer from said first supply conduit to an edge of said first substrate layer.

4. The method of claim 3 wherein said step of forming said second channel comprises the steps of:
    providing said second member as a second multi-layer segment having a second substrate layer;
    forming said second channel-defining layer having said well controlled thickness on a top surface of said second substrate layer;
    forming a second top layer having a controlled thickness on a side of said second channel-defining layer opposite said second substrate layer;
    selectively removing a portion of at least one of said second substrate layer and said second top layer, thereby creating a second supply conduit; and
    forming a second path through said second channel-defining layer from said second supply conduit to an edge of said second substrate layer.

5. The method of claim 4 wherein said step of positioning comprises the step of abutting said edge of said first multi-layer segment in non-parallel alignment against said edge of said second multi-layer segment such that said first channel and said second channel are aligned along a minor region of contact between said edges.

6. The method of claim 5 further comprising a step of sealing said edge of said first multi-layer segment to said edge of said second multi-layer segment such that matter introduced into said first supply conduit passes to said second supply conduit via said first channel and said second channel.

7. The method of claim 6 further comprising the steps of:
    attaching a first reservoir to said first supply conduit; and
    attaching a second reservoir to said second supply conduit.

8. The method of claim 1 wherein said steps of forming said first channel and enabling fluid communication include the steps of:
    providing said first member as a first substrate layer;
    removing a portion of said first substrate layer to form a first recess having side walls and a base;
    forming said first channel-defining layer having said well controlled thickness on at least said side walls and said base of said first recess, thereby defining a first coated tub;

configuring a first top layer within said first coated tub such that a top surface of said first top layer is generally coplanar with said top surface of said first substrate layer;

removing a portion of said first substrate layer via a bottom surface opposite said top surface of said first substrate layer such that said first channel-defining layer is exposed, thereby creating a first supply conduit; and selectively removing said first channel-defining layer from said first recess, thereby creating a first path extending from said first supply conduit to said top surface of said first substrate layer.

9. The method of claim 8 wherein said step of forming said second channel comprises the steps of:

providing said second member as a second substrate layer;

removing a portion of said second substrate layer to form a second recess having side walls and a base;

forming said second channel-defining layer having said well controlled thickness on at least said side walls and said base of said second recess, thereby defining a second coated tub;

configuring a second top layer within said second coated tub such that a top surface of said second top layer is generally coplanar with said top surface of said second substrate layer;

removing a portion of said second substrate layer via a bottom surface opposite said top surface of said second substrate layer such that said second channel-defining layer is exposed, thereby creating a second supply conduit; and selectively removing said second channel-defining layer from said second recess, thereby creating a second path extending from said second supply conduit to said top surface of said second substrate layer.

10. The method of claim 9 further comprising a step of bonding said top surface of said first substrate layer to said top surface of said second substrate layer such that said first path and said second path intersect in one location, wherein matter introduced into said first supply conduit passes through said first path to said second path via said one location.

11. The method of claim 10 further comprising the steps of:

attaching a first reservoir to said first supply conduit; and attaching a second reservoir to said second supply conduit.

12. A method of forming a nanopore comprising the steps of:

forming a first multi-layer segment having a first top layer and a first intermediate layer;

forming a second multi-layer segment having a second top layer and a second intermediate layer;

forming a first channel though said first intermediate layer, said first channel having a longitudinal direction;

forming a second channel through said second intermediate layer, said second channel having a longitudinal direction; and bonding said first and second multilayer multi-layer segments with said longitudinal directions being misaligned relative to each other such that an intersection of said first channel and said second channel defines boundaries of said nanopore.

13. The method of claim 12 wherein said step of forming said first channel includes the steps of:

(a) etching a portion of at least one of a first supporting semiconductor substrate layer and said first top layer, thereby creating a first supply conduit, said first supply conduit extending from an exterior surface of said first multi-layer segment to said first intermediate layer; and (b) etching said first intermediate layer from said first supply conduit to an edge of said first multi-layer segment;

and wherein said step of forming said second channel includes the steps of:

(a) etching a portion of at least one of a second supporting semiconductor substrate layer and said second top layer, thereby creating a second supply conduit, said second supply conduit extending from an exterior surface of said second multi-layer segment to said second intermediate layer; and (b) etching said second intermediate layer from said second supply conduit to an edge of said second multi-layer segment.

14. The method claim 13 further comprising the steps of:

orienting an edge of said first multi-layer segment in a non-parallel manner relative to an edge of said second multi-layer segment such that said first channel and said second channel intersect in a minor region of said edges; and sealing a portion of said first channel and a portion of said second channel such that matter intended to pass from said first supply conduit to said second supply conduit via said first channel and said second channel must pass through said nanopore.

15. The method of claim 12 wherein said step of forming said first multi-layer segment comprises the steps of:

(a) providing a first semiconductor substrate layer;

(b) etching a portion of said first semiconductor substrate layer to form a first recess having walls extending downwardly from a top surface of said first semiconductor substrate layer;

(c) forming a first intermediate layer having a controlled thickness on at least said walls and a base of said first recess, thereby defining a first coated tub;

(d) providing a first top layer within said first coated tub and exposing a periphery of said first intermediate layer;

(e) etching a portion of a bottom surface opposite said top surface such that said first intermediate layer is exposed, thereby creating a first supply conduit; and (f) selectively etching said first intermediate layer to create said first channel extending from said first supply conduit to said top surface of said first substrate layer;

and wherein said step of forming said second multilayer wafer comprises the steps of:

(a) providing a second semiconductor substrate layer;

(b) etching a portion of said second semiconductor substrate layer to form a second recess having walls extending downwardly from a top surface of said second semiconductor substrate layer;

(c) forming a second intermediate layer having a controlled thickness on at least said walls and a base of said second recess, thereby defining a second coated tub;

(d) providing a second top layer within said second coated tub and exposing a periphery of said second intermediate layer;

(e) etching a portion of a bottom surface opposite said top surface of said second semiconductor substrate layer such that said second intermediate layer is exposed, thereby creating a second supply conduit; and (f) selectively etching said second intermediate layer to create said second channel extending from said second supply conduit to said top surface of said second semiconductor substrate layer.

16. The method of claim 15 wherein said step of bonding includes aligning said first and second multi-layer segments such that said first channel intersects said second channel in one location.

17. A method of forming an opening having a well controlled geometry comprising the steps of:

forming a first segment, said first segment including a first top layer having predetermined dimensions, a first intermediate layer having predetermined dimensions and a first base layer, said first intermediate layer being located between said first top layer and said first base layer;

forming a second segment, said second segment including a second top layer having predetermined dimensions, a second intermediate layer having predetermined dimensions and a second base layer, said second intermediate layer being located between said second top layer and said second base layer;

forming a first path in said first intermediate layer;

forming a second path in said second intermediate layer; and bonding said first segment relative to said second segment such that an intersection of said first path with said second path defines the boundaries of said opening.

18. The method of claim 17 further comprising a step of tailoring properties at said opening by forming an oxide layer along said first and second paths.

19. The method of claim 18 wherein said tailoring step includes introducing at least one of agents and probes into said oxide layer, where said at least one is selected for enabling chemical analysis and characterization of macromolecules, synthetic and naturally occurring, colloidal micro and nanoparticles, based on interactions of such molecules and particles with the nanopore.

20. The method of claim 17 wherein said step of forming said first path comprises the steps of:

(a) etching a first conduit to said first intermediate layer; and (b) etching said first path through said first intermediate layer from said first conduit to an edge of said first segment;

and wherein said step of forming said second path includes the steps of:

(a) etching a second conduit to said second intermediate layer; and (b) etching a second path through said second intermediate layer from said second conduit to an edge of said second segment;

said method further comprising the steps of:

(a) orienting said edge of said first segment in a non-parallel manner relative to said edge of said second segment such that said first path and said second path are aligned in one location; and (b) sealing a portion of said first path and a portion of said second path such that matter intended to pass from said first conduit to said second conduit via said first path and said second path must pass through said opening.

21. The method of claim 17 wherein said step of forming said first segment comprises the steps of:

(a) forming a first recess within said first segment, said first recess having walls extending downwardly from a top surface of said first segment;

(b) forming said first intermediate layer having a controlled thickness at least on said walls and a base of said first recess, thereby defining a first tub;

(c) filling said first tub with a first top layer such that a top surface of said first top layer is coplanar with said top surface of said first segment;

(d) removing a portion of said first segment from a bottom surface opposite said top surface such that said first intermediate layer is exposed, thereby creating a first conduit; and (e) selectively removing said first intermediate layer to form said first path extending from said first conduit to said top surface of said first segment;

and wherein said step of forming said second segment comprises the steps of:

(a) forming a second recess within said second segment, said second recess having walls extending downwardly from a top surface of said second segment;

(b) forming said second intermediate layer having a controlled thickness at least on said walls and a base of said second recess, thereby defining a second tub;

(c) filling said second tub with said second top layer such that a top surface of said second top layer is coplanar with said top surface of said second segment;

(d) removing a portion of said second segment from a bottom surface opposite said top surface of said second segment such that said second intermediate layer is exposed, thereby creating a second conduit; and (e) selectively removing said second intermediate layer to form said second path extending from said second conduit to said top surface of said second segment;

and wherein said step of bonding includes bonding said top surface of said first segment to said top surface of said second segment such that said first path and said second path are aligned at one location, said one location being a nanopore.

22. A nanopore-defining device comprising:

a first multi-layer segment having a sequence of layers that includes two layers that are spaced apart to define a first surface slot having a first longitudinal direction, said first multi-layer segment having an interior path to said first surface slot; and a second multi-layer segment having a sequence of layers that includes two layers that are spaced apart to define a second surface slot having a second longitudinal direction, said second multi-layer segment having an interior path to said second surface slot, wherein said first and second multi-layer segments are connected such that said first surface slot is adjacent to and in fluid communication with said second surface slot, while said first longitudinal direction is misaligned with said second longitudinal direction.

23. The nanopore-defining device of claim 22 wherein said first and second surface slots extend along edges of said first and second multi-layer segments, respectively, said first and second surface slots being channels defined by partially etched interior layers, said edges being bonded to each other in a non-parallel relationship, said first longitudinal direction being coincident with a length of said edge of said first multi-layer segment, said second longitudinal direction being coincident with a length of said edge of said second multi-layer segment.

24. The nanopore-defining device of claim 22 wherein each of said first and second multi-layer segments includes a substrate layer having opposed major first and second sides, each of said first and second surface slots being along the respective first side and extending into the respective first and second multi-layer segment at an angle to said respective first side, said first side of said first multi-layer segment being bonded to said first side of said second multi-layer segment.

25. The nanopore-defining device of claim 24 wherein said two layers that are spaced apart to define said first surface slot are said substrate layer and a second layer that is seated within said substrate layer of said first multi-layer segment, said second layer having a major surface region that is substantially coplanar with said first side of said substrate layer of said first multi-layer segment.

26. The nanopore-defining device of claim 25 wherein said two layers that are spaced apart to define said second surface slot are said substrate layer and a second layer that is seated within said substrate layer of said second multi-layer segment, said second layer of said second multi-layer segment having a major surface region that is substantially coplanar with said first side of said substrate layer of said second multi-layer segment.

27. A method of forming a pore comprising the steps of:

forming members having elongated slots; and connecting said members so that said elongated slots are adjacent and are intentionally oriented into a non-parallel relationship to each other such that said pore has dimensions that are defined by a partial overlap of said elongated slots.

28. The method of claim 27 wherein said step of connecting sets a maximum cross sectional dimension of said pore at 0.1 millimeter.

29. The method of claim 27 wherein said step of connecting is implemented such that said elongated slots are more orthogonal than parallel.

30. The method of claim 27 wherein said step of forming includes providing said elongated slots along edges of said members and includes providing flow paths between said elongated slots and openings into interiors of said members.

31. The method of claim 27 wherein said step of forming includes providing said elongated slots along generally planar major surfaces of said members and wherein said step of connecting includes bonding said members to each other along said generally planar major surfaces.

* * * * *